United States Patent
Mans et al.

(10) Patent No.: US 10,321,685 B2
(45) Date of Patent: Jun. 18, 2019

(54) BIOCIDE-FREE PREWETTED SPONGE CLOTH

(71) Applicant: Kalle GmbH, Wiesbaden (DE)

(72) Inventors: Leo Mans, Mainz (DE); Norbert Tüschen, Wiesbaden (DE); Marian Peter Sklorz, Ingelheim (DE)

(73) Assignee: Kalle GmbH, Wiesbaden (DE)

( * ) Notice: Subject to any disclaimer, the term of this patent is extended or adjusted under 35 U.S.C. 154(b) by 0 days.

(21) Appl. No.: 14/967,566

(22) Filed: Dec. 14, 2015

(65) Prior Publication Data

US 2016/0174564 A1  Jun. 23, 2016

(30) Foreign Application Priority Data

Dec. 23, 2014  (DE) ........................ 10 2014 019 540

(51) Int. Cl.
*A01N 59/06* (2006.01)
*A01N 25/34* (2006.01)
*D06M 11/11* (2006.01)
*D06M 11/56* (2006.01)
*D06M 13/144* (2006.01)
*D06M 13/148* (2006.01)
*D06M 15/03* (2006.01)
*D06M 15/09* (2006.01)
*D06M 15/263* (2006.01)
*D06M 15/267* (2006.01)
*D06M 15/356* (2006.01)
*D06M 15/507* (2006.01)
*D06M 16/00* (2006.01)
*D06M 101/06* (2006.01)

(52) U.S. Cl.
CPC ............. *A01N 59/06* (2013.01); *A01N 25/34* (2013.01); *D06M 11/11* (2013.01); *D06M 11/56* (2013.01); *D06M 13/144* (2013.01); *D06M 13/148* (2013.01); *D06M 15/03* (2013.01); *D06M 15/09* (2013.01); *D06M 15/263* (2013.01); *D06M 15/267* (2013.01); *D06M 15/3562* (2013.01); *D06M 15/507* (2013.01); *D06M 16/00* (2013.01); *D06M 2101/06* (2013.01)

(58) Field of Classification Search
CPC .................................................... A01N 59/06
See application file for complete search history.

(56) References Cited

U.S. PATENT DOCUMENTS

| | | | | |
|---|---|---|---|---|
| 8,343,522 B2 * | 1/2013 | Pohl | ........................ | A01N 37/46 424/402 |
| 2009/0163598 A1 * | 6/2009 | Truong | .................. | A01N 47/44 514/635 |
| 2011/0232018 A1 * | 9/2011 | Mans | ...................... | A47L 13/16 15/209.1 |
| 2013/0053353 A1 * | 2/2013 | Tamarkin | .................. | A61K 8/31 514/152 |

FOREIGN PATENT DOCUMENTS

| | | | |
|---|---|---|---|
| DE | 29618058 U1 | | 3/1997 |
| EP | 2085138 | * | 1/2009 |
| EP | 2 363 024 A2 | | 9/2011 |
| EP | 2368936 A2 | | 9/2011 |
| WO | WO 2006/010273 A1 | | 2/2006 |
| WO | WO 2009/085570 A2 | | 7/2009 |

OTHER PUBLICATIONS

Mickey Parish, "How do salt and sugar prevent microbial spoilage?" Feb. 21, 2006, http://www.scientificamerican.com/article/how-do-salt-and-sugar-pre/.

* cited by examiner

*Primary Examiner* — Adam C Milligan
*Assistant Examiner* — Sarah Alawadi
(74) *Attorney, Agent, or Firm* — ProPat, L.L.C.; Cathy R. Moore; Vinisha Joshi

(57) ABSTRACT

A biocide-free sponge cloth prewetted with a hygroscopically acting inorganic salt is provided. The spone cloth is based on regenerated cellulose which is mechanically reinforced with fibers and/or a web and includes a hygroscopically acting salt. The sponge cloth has an $a_w$ value of less than 0.80. On account of the low $a_w$ value, the sponge cloth has an antibacterial, bacteriostatic, fungicidal and/or fungistatic effect. The hygroscopically acting salt is preferably magnesium chloride. It can be combined with further inorganic salts, with low molecular weight, mono- or polyhydric alcohols, with sugars, sugar esters, mono- or polybasic carboxylic acids, esters of mono- or polybasic carboxylic acids and/or with hydrophilic polymers. The sponge cloth is preferably produced by the viscose process.

11 Claims, No Drawings

BIOCIDE-FREE PREWETTED SPONGE CLOTH

CROSS-REFERENCE TO RELATED APPLICATIONS

This application claims priority to German Patent Application No. 10 2014 019 540.6 filed Dec. 23, 2014, which is hereby incorporated herein by reference in its entirety.

FIELD OF THE INVENTION

The invention relates to a prewetted, fungicide- and/or bactericide-free finished sponge cloth based on regenerated cellulose which is mechanically reinforced with internal fibres and/or a web.

BACKGROUND OF THE INVENTION

Sponge cloths based on regenerated cellulose with mechanical reinforcement of fibres and/or a web are known (see EP 2 368 936 A2). Dry sponge cloths of this type are relatively hard, those with web reinforcement can even break as a result of bending. Consumers prefer the relatively soft, prewetted sponge cloths over the dry hard ones. Moreover, these have relatively more volume and a soft feel. For this, the sponge cloths are generally treated with an aqueous solution of a hygroscopically acting salt, in particular with a magnesium chloride solution. However, a disadvantage of such prewetted sponge cloths is their tendency towards mould infestation, particularly if they are in an air-tight film pack. In order to counteract this, prewetted sponge cloths have hitherto been finished with a biocide. This substance is generally added here to the magnesium chloride solution. The magnesium chloride, as well as some of the biocide, are washed out upon using the sponge cloth for the first time. Nevertheless, the presence of such an active ingredient, or more generally of a biocide, will in future have to be noted on the sales packaging of the sponge cloth. This may constitute a sales hindrance. Moreover, the use of biocides in sponge cloths has to be approved, there being a considerably restrictive tendency for approval.

DE 296 18 058 U1 discloses sponge cloths which are produced by the viscose process and which are provided with a biocide. Also known is a sterilization of dry sponge cloths with gamma rays or peroxides.

SUMMARY OF ADVANTAGEOUS EMBODIMENTS OF THE INVENTION

It is therefore the object to provide a prewetted sponge cloth which is protected in a different way than with a biocide against infestation with mould fungi and other microorganisms. "Protected" means here that the microorganisms are killed off or at least their growth is inhibited.

A prerequisite for the growth of microorganisms is the presence of active, free water in the sponge cloth. A measure of the freely available water in a material is the $a_w$ value. It is defined as the quotient of the water vapour pressure of the material divided by the water vapour pressure of the water, measured in each case at the same temperature.

The $a_w$ value is between 0 and 1, with pure water having an $a_w$ value of 1. Absolutely water-free materials have an $a_w$ value of 0. Bacteria require an $a_w$ value of at least 0.91 in order to be able to replicate. *Staphylococcus aureus* can also survive at an $a_w$ value of 0.86 to 0.90. For replication, yeasts require at least an $a_w$ value of 0.88 to 0.94, whereas mould fungi are able to grow even at an $a_w$ value of 0.80 to 0.85. For prewetted sponge cloths with an $a_w$ value of more than 0.80, therefore, there is the risk that the stated microorganisms will spread. This is true particularly if the sponge cloths are in a water-vapour-tight packaging and the storage temperature is increased.

DETAILED DESCRIPTION OF ADVANTAGEOUS EMBODIMENTS OF THE INVENTION

The aforementioned object can therefore be achieved in full scope if the fraction of freely available water in the sponge cloth is reduced such that the as value is less than 0.80. The other properties of the sponge cloth, in particular the wet thickness and the mechanical stability, should not be adversely affected by this measure.

The present application therefore provides a biocide-free sponge cloth prewetted with a hygroscopically acting inorganic salt and based on regenerated cellulose which is mechanically reinforced with fibres and/or a web, characterized in that it comprises at least one substance selected from the group consisting of inorganic salts, mono- or polyhydric, low molecular weight, aliphatic alcohols, sugars, sugar esters, mono- or polybasic carboxylic acids, esters of mono- or polybasic carboxylic acids and hydrophilic polymers in an amount which suffices to establish an $a_w$ value of less than 0.8 in the sponge cloth.

The sponge cloth according to the invention comprises no fungicide, bactericide or other biocide which is declarable according to Annex II, part 1 of the Commission Delegated Regulation (EU) No. 1062/2104 dated Aug. 4, 2014, on the work programme for the systematic examination of all existing active substances contained in biocidal products referred to Regulation (EU) No. 528/2012 for protecting agents for products during storage and for protecting agents for fibers, leather, gummi and polymerized materials, i.e. for product types 6 and 9 the version valid on the application date of the present application. A copy of Annex II, part 1 of this Regulation is attached to this application. In connection with the present invention, such a sponge cloth is referred to as "biocide-free".

The sponge cloth according to the invention is generally produced by the viscose process. The process is described for example in the German Patent 807 439. In this process, viscose is mixed with Glauber's salt crystals to give a sponge cloth crude mass. Relatively short fibres (length of the fibres about 2 mm to 30 mm, preferably 3 to 6 mm) can also be added to the crude mass. The fibres are often cotton fibres (preferably cotton noils), but it is also possible to use fibres made of other natural and/or synthetic polymers. The fibres must not be attacked too much by the strongly alkaline viscose. The sponge cloth crude mass is applied as a flat layer to a rotating, perforated conveyor belt and conveyed on the conveyor into a heated precipitation and regeneration bath in which the cellulose is regenerated from the viscose. The Glauber's salt has a relatively low melting point of 32 to 33° C. It therefore melts in the heated precipitation and regeneration bath and is dissolved out. Corresponding pores or cavities are left behind in the sponge cloth. The crude sponge cloth is then conveyed through various washing baths and (for prewetting) through a bath with a solution of a hygroscopic salt, in particular an aqueous magnesium chloride solution. Excess liquid is then removed from the sponge cloth with the aid of a pair of nip rolls.

The water fraction in the sponge cloth according to the invention is generally 75 to 200% by weight, preferably 100 to 150% by weight, in each case based on the dry weight of the sponge cloth. It consequently has a very soft and pleasant "feel", which is particularly valued by consumers.

The sponge cloth crude mass—with or without fibres—can also be applied as a thin layer to one or both sides of a web. The web usually consists of polyester or cotton. The web coated with the crude mass is then conveyed through precipitation, regeneration and washing baths.

It has been found that the $a_w$ value can be reduced in different ways. In one embodiment of the invention, the $a_w$ value in the sponge cloth is reduced below the value of 0.80 by adding at least one further inorganic salt besides the hygroscopic salt serving as softener. The additional salt is, for example, lithium chloride, sodium chloride (cooking salt), potassium chloride, sodium sulphate, magnesium sulphate or calcium sulphate. The further inorganic salt generally does not have a hygroscopic action. The fraction of the further inorganic salt is expediently 10 to 30% by weight, preferably 15 to 25% by weight, in each case based on the dry weight of the sponge cloth.

In general, the further salt is applied in the form of a solution together with the solution of the magnesium chloride, for example by conveying the sponge cloth through an impregnation tank with a solution of the different salts. The salt concentration is chosen such that the am value drops below 0.80.

The table below summarizes the $a_w$ values of saturated solutions of different salts:

| Salt | LiCl | MgCl$_2$ | K$_2$CO$_3$ | Mg(NO$_3$)$_2$ | NaBr | SrCl$_2$ | NaCl | KCl |
| --- | --- | --- | --- | --- | --- | --- | --- | --- |
| $a_w$ value | 0.112 | 0.327 | 0.438 | 0.529 | 0.577 | 0.708 | 0.753 | 0.843 |

The solvent used in the solution of the various salts can be water, but is particularly advantageously a mixture of water and mono- or polyhydric, low molecular weight alcohols.

Low molecular weight alcohols in connection with the present invention are alcohols with up to 6 carbon atoms which, besides the carbon atoms, comprise only also oxygen and hydrogen atoms and have exclusively hydroxy groups as functional groups. The mono- or polyhydric alcohols are in particular ethanol, n-propanol, isopropanol, ethylene glycol (ethanediol), diethylene glycol, propane-1,2- or -1,3-diol or mixtures thereof. In connection with the present application, a polyhydric alcohol is to be understood as meaning an alcohol with up to 8 hydroxy groups, preferably with up to 6 hydroxy groups.

In a further embodiment, the fraction of the hygroscopically acting inorganic salt, preferably of the magnesium chloride, is increased beyond the fraction known hitherto until an $a_w$ value of less than 0.8 is reached. This is reached for example by impregnating the sponge cloth with a 20 to 22% strength by weight aqueous magnesium chloride solution. The fraction of magnesium chloride cannot increase significantly above 22% by weight since the solution is otherwise too viscous and is only poorly absorbed by the sponge cloth.

Mono- or polyhydric, low molecular weight alcohols likewise reduce the $a_w$ value in the sponge cloth. If such alcohols are used, then the salt fraction in the sponge cloth can be reduced. The further inorganic salt can then be dispensed with entirely.

Finally, a reduction in the $a_w$ value to less than 0.80 can also be achieved by adding sugars, sugar esters, mono- or polybasic carboxylic acids, esters of mono- or polybasic carboxylic acids or mixtures thereof. The sugars are generally mono- or disaccharides. The fraction of sugars or sugar esters is such that the sponge cloth is not sticky and that the pores of the sponge cloth remain open. The specified agents can be combined with salts and/or the mono- or polyhydric alcohols.

Finally, the sponge cloth according to the invention can also comprise hydrophilic polymers. These too contribute to the lowering of the $a_w$ value. Suitable hydrophilic polymers are oligo- and polysaccharides, and derivatives thereof, for example fructans and levans, chitosan, carrageenan, pectins and alginates, and derivatives thereof, for example propylene glycol alginate. Also of suitability are cellulose ethers, such as carboxyalkylcellulose (for example carboxymethylcellulose), hydroxyalkylcellulose (for example hydroxyethyl- and hydroxypropylcellulose) and alkylhydroxyalkylcellulose (for example methylhydroxyethylcellulose and ethylhydroxypropylcellulose). Also of suitability are synthetic hydrophilic polymers, such as polyvinylpyrrolidone and copolymers with vinylpyrrolidone units, polymers of and copolymers with units of dimethylaminoethyl (meth)acrylates, poly(meth)acrylic acid and polylactides. The solubility of the hydrophilic polymers in water can, if required, be adjusted with low molecular weight crosslinkers, such as glyoxylic acid ("low molecular weight" in this connection means a molecular weight of less than 300 g/mol). The fraction of hydrophilic polymers can be up to 15% by weight, preference being given to a fraction of 5 to 10% by weight, in each case based on the dry weight of the sponge cloth.

In the sponge cloth according to the invention, $a_w$-value-reducing agents from two or more of the groups described above can be combined. In each case it has an $a_w$ value of less than 0.80 and accordingly no longer requires a declarable biocide.

The examples below serve to illustrate the invention. Percentages therein are to be understood as meaning percentages by weight, unless stated otherwise or directly evident from the context.

To determine the $a_w$ value, an $a_w$ value meter, model 5803.056, from G. Lufft Mess- und Regeltechnik GmbH, D-70736 Fellbach, was used. Calibration of the instrument was carried out with special paper, which was wetted until dripping wet with a saturated aqueous barium chloride solution, at a temperature of 20° C. During the measurement, the definitive $a_w$ value was established after about 2.5 to 3 hours at a constant temperature. For a fluctuating measurement temperature, the $a_w$ value valid for 20° C. was ascertained by means of the correction table accompanying the instrument. For a deviation of ±1° C., a correction of the $a_w$ value of ±0.002 is to be taken into consideration. The correction table is valid in the range from 15 to 25° C. All of the $a_w$ values specified in the examples below and in the other parts of the present application refer to a temperature of 20° C.

Example 1 (Sponge Cloth Impregnated with Magnesium Chloride Solutions of Varying Concentration, without Biocide)

A sponge cloth produced by the viscose process with reinforcement made of cotton fibres was placed into aqueous magnesium chloride solutions of differing concentration and then squeezed in order to remove excess solution. The sponge cloths impregnated with the magnesium chloride solutions of increasing concentration are referred to below as Samples 1 to 5. Aqueous solutions which comprise more than 22% by weight of MgCl$_2$ were no longer adequately absorbed by the sponge cloth.

| Sample No. | Fraction of MgCl$_2$ in the solution [% by weight] | $a_w$ value |
| --- | --- | --- |
| 1 | 16.1 | 0.85 |
| 2 | 18.1 | 0.825 |
| 3 | 20.0 | 0.78 |
| 4 | 22.0 | 0.75 |

The antimicrobial properties of the individual samples were investigated in accordance with the method AATCC 100.

For this, in each case 0.5 ml of a suspension of *Escherichia coli* (DSM 1576) in a 0.9% strength aqueous NaCl solution was applied to the individual sponge cloth test pieces (edge length 2 cm) and the samples were stored individually in sterile Petri dishes at a temperature of 36° C. for 24 hours. Then, the germs were removed from the test pieces in 10 ml of BD D/E neutralization solution, and the germ count was determined by means of plate pouring. All investigations were performed as a triple determination. An additional sterilization of the samples was not carried out.
Nutrient medium: CASO-agar
Incubation time: 2 days The data reveal that the maximum antimicrobial efficacy is only reached when the sponge cloth was impregnated with a 20 to 22% strength by weight aqueous $MgCl_2$ solution.

Example 2 (Sponge Cloth Impregnated with Magnesium Chloride Solution without Additional Biocide and Sponge Cloth Impregnated with a Softener Solution which Comprises Magnesium Chloride and a Biocide)

Samples of the following prewetted sponge cloths were investigated:

| Sample | Softener solution | Colour/width of the sponge cloth [mm] | $MgCl_2$ concentration in the softener solution [% by weight] | $a_w$ value | Type of biocide or fungicide | Amount of biocide or fungicide |
|---|---|---|---|---|---|---|
| 1 | $MgCl_2$ + demin. water | yellow/180 | 18.30 | 0.82 | Vantocil ® IB Microbiocide 20% | 10 g of fungicide in 2000 g of solution, ca. 1000 ppm |
| 2 | $MgCl_2$ + demin. water | red/180 | 18.30 | 0.82 | Omacide ® IPBC 30 DPG, ca. 30% | 7 g of fungicide in 2000 g of solution, ca. 1000 ppm |
| 3 | $MgCl_2$ + demin. water | blue/180 | 18.30 | 0.82 | Bardac ® 2240, 12.50% | 16 g of fungicide in 2000 g of solution, ca. 1000 ppm |
| 4 | $MgCl_2$ + demin. water | turquoise/180 | 18.30 | 0.82 | — | — |
| 5 | $MgCl_2$ + factory water | white/180 | 18.30 | 0.82 | — | — |

The decrease in germ count was calculated as follows:
Based on the starting germ count:

$$\% \text{ decrease} = \frac{(T_0 - T_x)}{T_0} \times 100$$

where
$T_0$ is the germ count per test piece directly after inoculation, and
$T_x$ is the germ count per test piece after incubation for 24 hours.
The results are summarized in the table below:

| Sample No. | Contact time [h] 0 = starting value | CFU*/test piece | Average value reduction [%] | Standard deviation [%] |
|---|---|---|---|---|
| 1 | 0 | $1.15 \times 10^5$ | — | — |
|   | 24 | $2.01 \times 10^4$ | 81.30 | 8.03 |
| 2 | 0 | $1.11 \times 10^5$ | — | — |
|   | 24 | $9.00 \times 10^3$ | 91.64 | 1.86 |
| 3 | 0 | $1.08 \times 10^5$ | — | — |
|   | 24 | $8.53 \times 10^3$ | 92.07 | 1.34 |
| 4 | 0 | $9.87 \times 10^5$ | — | — |
|   | 24 | $7.17 \times 10^3$ | 93.34 | 1.15 |

*CFU = colony-forming unit

The resistance of the samples to the mould fungus *Aspergillus niger* (DSM 1957) was tested. The testing was performed in accordance with DIN 53 931.

"Demin. water" stands for demineralized water.

For this, a spore suspension of the mould fungus was applied to growth-promoting nutrient media and incubated for 24 hours in order to permit germination of the spores. Then, round test pieces of the samples with a diameter of 4 cm were laid out on the inoculated nutrient media. After storage for 14 days at 29±1° C. under humid conditions, a visual and macroscopic assessment of the mould fungus growth on the test pieces and the surrounding nutrient medium was made.

All of the test pieces exhibited a zone of inhibition formation (growth-free zone in the vicinity of the sample). Considerable growth with mould fungi and considerable spore formation was evident on the surface of the surrounding nutrient medium.

The experiments reveal that the addition of a biocide does not improve the resistance of the sponge cloth to mould fungi if the concentration of magnesium chloride in the softener solution is sufficiently high. The use of factory water instead of demineralized water (demin. water) did not lead to any changes in the fungicidal properties.

Example 3 (Sponge Cloths Impregnated with a Mixture of MgCl$_2$ and Other Salts)

| Sample | Salts in the aqueous softener solution | Colour/width of the sponge cloth | Concentration in the softener solution (% by weight) | $a_w$ value | Composition of the mixture |
|---|---|---|---|---|---|
| 6 | MgCl$_2$ + NaCl | yellow/210 mm | MgCl$_2$, 30% strength 1 kg NaCl + 3 l demin. water | 0.71 | 3780 ml MgCl$_2$ + 2850 ml NaCl solution |
| 7 | MgCl$_2$ + Na$_2$SO$_4$ | orange/180 mm | MgCl$_2$, 30% strength 500 g Glauber's salt + 3 l demin. water | 0.82 | 3780 ml MgCl$_2$ + 2850 ml Na$_2$SO$_4$ solution |

The resistance of the samples to the mould fungus *Aspergillus niger* (DSM 1957) was carried out in accordance with DIN 53 931, as described in Example 2. However, this type of loading is extreme and thus does not arise under conditions in practice.

In the case of Sample 6, after storage for one week, considerable growth with considerable spore formation from the edge inwards emerged (less than 25% of the sample surface was covered in growth); after storage for 2 weeks, the sample surface was completely (100%) covered in growth.

In the case of Sample 7, after storage for one week the sample was covered with considerable growth from the edge inwards with considerable spore formation (less than 25% of the sample surface was covered in growth); after storage for 2 weeks, the sample surface was covered in growth with individual colonies (25 to 75% of the sample surface was covered in growth). The results reveal that the antimicrobial efficacy is different depending on the type of salt.

In addition, the antimicrobial efficacy of the samples towards *Staphylococcus aureus* (DSM 799) and *Escherichia coli* (DSM 1576) was tested, as described in Example 1. The test results are summarized in the tables below.

Test germ *Staphylococcus aureus*:

| Sample No. | Contact time [h] | CFU/test piece | Average value reduction [%] | Standard deviation [%] |
|---|---|---|---|---|
| 6 | 0 | 1.51 × 10$^5$ | — | — |
|   | 24 | 7.3 × 10$^2$ | 99.53 | 0.08 |
| 7 | 0 | 1.46 × 10$^5$ | — | — |
|   | 24 | <10 | ≥99.99 | 0.00 |

Test germ *Escherichia coli*:

| Sample No. | Contact time [h] | CFU/test piece | Average value reduction [%] | Standard deviation [%] |
|---|---|---|---|---|
| 6 | 0 | 1.01 × 10$^5$ | — | — |
|   | 24 | 1.30 × 10$^3$ | 98.94 | 0.09 |
| 7 | 0 | 7.97 × 10$^4$ | — | — |
|   | 24 | 1.67 × 10$^1$ | 99.98 | 0.01 |

For comparison, the an value was determined on hitherto customary sponge cloths prewetted with magnesium chloride solutions of differing concentration from the applicant which are all produced by the viscose process and comprise cotton fibres as mechanical reinforcement but no web. The values are summarized in the table below. Also contained are the data for a sponge cloth which has been wetted just with water.

| No. | MgCl$_2$ content [%] | $a_w$ value | Weight air dry/damp [g] | Width/length [mm] | Area [m$^2$] | Thickness damp [mm] | Weights per area dry/damp/MgCl$_2$ solution [g/m$^2$] |
|---|---|---|---|---|---|---|---|
| 1 | 0 | 0.92 | 1.73/5.7 | — | 0.0063 | 4.65 | 275/902/627 |
| 2 | 8.1 | 0.89 | 8.54/19.54 | 178.5/199.25 | 0.0356 | 5.5 | 240/549/309 |
| 3 | 16.1 | 0.85 | 8.54/21.19 | 179/198 | 0.0354 | 5.7 | 241/598/357 |
| 4 | 18.1 | 0.83 | 8.58/21.85 | 179/199 | 0.0356 | 5.8 | 241/614/373 |

Finally, the $a_w$ value of prewetted cellulose sponge cloths originating from competitors was also determined. The magnesium chloride content in these sponge cloths is not stated and was not determined.

| No. | MgCl$_2$ content [%] | $a_w$ value | Weight air dry/damp [g] | Width/length [mm] | Area [m$^2$] | Thickness damp [mm] | Weights per area dry/damp/MgCl$_2$ solution [g/m$^2$] |
|---|---|---|---|---|---|---|---|
| 5)[1] | n.s. | 0.88 | 10.33/30.22 | 190/204 | 0.0388 | 5.0-6.3 | 267/780/513 |
| 6)[2] | n.s. | 0.89 | 10.76/29.87 | 192/205 | 0.0394 | 5.4 | 273/759/486 |
| 7)[3] | n.s. | 0.84 | 9.31/32.74 | 181/199 | 0.0360 |  | 258/909/650 |
| 8)[4] | n.s. | 0.83 | —/5.55 | —/— | 0.0063 | 4.7 | —/870/— |

[1] Spontex AquaPur®, apple green
[2] Spontex AquaPur®, red
[3] Wettex® Vileda Original, yellow
[4] Wettex® Vileda Original, blue Excerpt from Annex II, Part 1 of the Regulation
(EU) No. 1062/2104 Dated Aug. 4, 2014

| Substance name | CAS-Number | 6 | 9 |
|---|---|---|---|
| Monohydrochloride of polymer of N,N'''-1,6-hexanediylbis[N'-cyanoguanidine] (EINECS 240-032-4) and hexamethylenediamine (EINECS 204-679-6)/Poly-hexamethylenbiguainde (monomer: 1,5-bis(trimethylen)-guanylguanidinium monohydrochloride) (PHMB) | 27083-27-8/32289-58-0 | x | x |
| Reaktion mass of titaniumdioxide and silver chloride | Nicht verfügbar | x | x |
| Mixture of 5-chloro-2-methyl-2H-isothiazol-3-one (Einecs 247-500-7) and 2-methyl-2H-isothiazol-3-one (Einecs 220-239-6) (Mixture of CMIT/MIT) | 55965-84-9 | x |  |
| cis-1-(3-chloroallyl)3,5,7-triaza-1-azonia-adamantane chloride (cis-CTAC) | 51229-78-8 | x |  |
| 2-butyl-benzo[d]isothiazol-3-one (BBIT) | 4.7.4299 | x | x |
| Sodium N-(hydroxymethyl)glycinate | 70161-44-3 | x |  |
| Didecyldimethylammoniumchloride | 68424-95-3 | x |  |
| 3,3'-Methylenebis[5-methyloxazolidine] (Oxazolidin/MBO) | 66204-44-2 | x |  |
| Tetrakis(hydroxymethyl)phosphonium-sulphate (2:1) (THPS) | 55566-30-8 | x |  |
| 2-Bromo-2-(bromomethyl)pentanedinitrile (DBDCB) | 35691-65-7 | x |  |
| 2-Octyl-2H-isothiazol-3-one (OIT) | 26530-20-1 | x | x |
| α,α',α''-Trimethyl-1,3,5-triazine-1,3,5(2H,4H,6H)-triethanol (HPT) | 25254-50-6 | x |  |
| Potassium (E,E)-hexa-2,4-dienoate (Potassium-Sorbate) | 24634-61-5 | x |  |
| p-[(Diiodomethyl)sulphonyl]toluene | 20018-09-1 | x | x |
| Sodium p-chloro-m-cresolate | 15733-17-9 | x | x |
| (Benzyloxy)methanol | 14548-60-8 | x |  |
| Potassium 2-biphenylate | 13707-65-8 | x | x |
| Dodecylguanidine monohydrochloride | 13590-97-1 | x |  |
| Pyrithione zinc (Zinc pyrithion) | 13463-41-7 | x | x |
| 2,2-Dibromo-2-cyanoacetamide (DBNPA) | 10222-01-2 | x |  |
| 7a-Ethyldihydro-1H,3H,5H-oxazolo[3,4-c]oxazole (EDHO) | 7747-35-5 | x |  |
| Hydrogen peroxide | 7722-84-1 | x |  |
| Didecyldimethylammonium chloride (DDAC) | 7173-51-5 | x |  |
| 1,3-Bis(hydroxymethyl)-5,5-dimethyl imidazolidin-2,4-dione (DMDMH) | 6440-58-0 | x |  |
| N,N'-Methylenbismorpholine (MBM) | 5625-90-1 | x |  |
| Tetrahydro-1,3,4,6-tetrakis(hydroxymethyl)imidazo[4,5-d]imidazole-2,5(1H,3H)-dione (TMAD) | 5395-50-6 | x |  |
| 2,2',2''-(Hexahydro-1,3,5-triazin-1,3,5-triyl)triethanol (HHT) | 4.4.4719 | x |  |
| Methenamite 3-chloroallylchloride (CTAC) | 4080-31-3 | x |  |
| Pyridin-2-thiol-1-oxide, sodium salt (Sodium pyrithione) | 3811-73-2 | x | x |
| (Ethylendioxy)dimethanol (Reaktion products of ethylene glycol with paraformaldehyde (EGForm)) | 3586-55-8 | x |  |
| 2-Methyl-2H-isothiazol-3-one (MIT) | 2682-20-4 | x |  |
| 1,2-Benzisothiazol-3(2H)-one (BIT) | 2634-33-5 | x | x |
| 2,2'-Dithiobis[N-methylbenzamide] (DTBMA) | 2527-58-4 | x |  |
| N-(3-aminopropyl)-N-dodecylpropane-1,3-diamine (Diamine) | 2372-82-9 | x |  |
| Tetrahydro-3,5-dimethyl-1,3,5-thiadiazine-2-thione (Dazomet) | 533-74-4 | x |  |
| Sodium 2-biphenylate | 132-27-4 | x | x |
| 2-Phenoxyethanol | 122-99-6 | x |  |
| Glutaral (Glutaraldehyde) | 111-30-8 | x |  |
| Hexa-2,4-dienoic acid (Sorbic acid) | 110-44-1 | x |  |
| Biphenyl-2-ol | 90-43-7 | x | x |
| L-(+)-Lactic acid | 79-33-4 | x |  |
| Peracetic acid | 79-21-0 | x |  |
| Formic acid | 64-18-6 | x |  |
| Chlorocresol | 59-50-7 | x | x |
| Bronopol | 52-51-7 | x | x |
| Potassium dimethyldithiocarbamate | 128-03-0 |  | x |
| Sodium dimethyldithiocarbamate | 128-04-1 |  | x |

-continued

| Substance name | CAS-Number | 6 | 9 |
|---|---|---|---|
| N-(Trichloromethylthio)phthalimide (Folpet) | 133-07-3 | | x |
| Thiuram | 137-26-8 | | x |
| Metam-sodium | 137-42-8 | | x |
| 2-(4-Thiazolyl)-1H-benzimidazol (Thiabendazol) | 148-79-8 | | x |
| Terbutryn | 886-50-0 | | x |
| Carbendazim | 10605-21-7 | | x |
| (Benzothiazol-2-ylthio)methylthiocyanate (TCMTB) | 21564-17-0 | | x |
| Dimethyloctadecyl[3-(trimethoxysilyl) propyl]ammonium chloride | 27668-52-6 | | x |
| Dimethyltetradecyl [3-(trimethoxysilyl) propyl]ammonium chloride | 41591-87-1 | | x |
| 3-Iodo-2-propinyl butylcarbamate (IPBC) | 55406-53-6 | | x |
| 4,5-Dichloro-2-octylisothiazol-3(2H)-one (4,5-Dichloro-2-octyl-2H-isothiazol-3-one (DCOIT)) | 64359-81-5 | | x |
| Silver sodium hydrogen zirconium phosphate | 265647-11-8 | | x |
| Silver zeolite | Entfallt | | x |
| Silver phosphate glass | 308069-39-8 | | x |
| Silver zink zeolite | 130328-20-0 | | x |
| Silver copper zeolite | 130328-19-7 | | x |
| Silver adsorbed on silicon dioxide (as a nanomaterial in the form of a stable aggregate with primary particles in the nanoscale) | Nicht verfügbar | | x |
| Polyhexamethylenbiguanide | 91403-50-8 | | x |

That which is claimed:

1. A biocide-free sponge cloth prewetted with a hygroscopically acting inorganic salt, said sponge cloth based on regenerated cellulose which is mechanically reinforced with fibres, with a web, or with a combination thereof,
    wherein the sponge cloth optionally comprises at least one substance selected from the group consisting of at least one further inorganic salt, sugars, sugar esters, monobasic or polybasic carboxylic acids, and hydrophilic polymers, with the hygroscopically acting inorganic salt and any optional substance(s) present in an amount which suffices in order to establish an $a_w$ value of less than 0.8 in the sponge cloth,
    wherein said sponge cloth is prewetted with an aqueous solution of magnesium chloride as said hygroscopically acting inorganic salt, wherein the fraction of said magnesium chloride is from 20% to 22% by weight based on the weight of the aqueous solution, and said aqueous solution further optionally comprises a polyhydric, low molecular weight, aliphatic alcohol.

2. Sponge cloth according to claim 1, wherein the further inorganic salt is lithium chloride, sodium chloride, potassium chloride, sodium sulphate, magnesium sulphate and/or calcium sulphate.

3. Sponge cloth according to claim 1, wherein the polyhydric, low molecular weight, aliphatic alcohol is ethanol, n-propanol, isopropanol, ethylene glycol, diethylene glycol, propane-1,2- or -1,3-diol or a mixture thereof.

4. Sponge cloth according to claim 1, wherein the hydrophilic polymer is an oligosaccharide, polysaccharide, a cellulose ether, or a synthetic hydrophilic polymer.

5. Sponge cloth according to claim 4, wherein the hydrophilic polymer is a fructan, a levan, chitosan, carrageenan, pectin, alginate, a carboxyalkylcellulose, a hydroxyalkylcellulose, an alkylhydroxyalkylcellulose, polyvinylpyrrolidone, dimethylaminoethyl (meth)acrylates, poly(meth)acrylic acid or polylactide.

6. Sponge cloth according to claim 5, wherein the alginate is propylene glycol alginate.

7. Sponge cloth according to claim 1, wherein the biocide free sponge cloth comprises a water fraction of 75 to 200% by weight, based on the dry weight of the biocide free sponge cloth.

8. Sponge cloth according to claim 7, wherein the biocide free sponge cloth comprises a water fraction of 100 to 150% by weight, based on the dry weight of the biocide free sponge cloth.

9. A method of producing a sponge cloth according to claim 1, wherein said method comprises
    producing viscose by the viscose process and
    mixing the viscose with Glauber's salt crystals to produce a sponge cloth crude mass and
    prewetting with an aqueous solution containing a hygroscopically acting inorganic salt
    the hygroscopically acting inorganic salt and any optional substance(s) present in an amount which suffices in order to establish an $a_w$ value of less than 0.8 in the sponge cloth,
    the hygroscopically acting inorganic salt is magnesium chloride and
    the fraction of said magnesium chloride is from 20% to 22% by weight based on the weight of the aqueous solution.

10. Sponge cloth according to claim 1, wherein said cloth exhibits an average value in germ count reduction of 92.07 to 93.34% for a 24 hour period, per the AATCC 100 test method.

11. A biocide-free sponge cloth prewetted with a hygroscopically acting inorganic salt, said sponge cloth based on regenerated cellulose which is mechanically reinforced with fibres, with a web, or with a combination thereof,
    wherein the sponge cloth comprises magnesium chloride and either $Na_2SO_4$ or NaCl, said salts present in a sufficient amount to establish an $a_w$ value of 0.82 or less in the sponge cloth,
    wherein said sponge cloth is prewetted with an aqueous solution of the magnesium chloride and either NaCl or $Na_2SO_4$, and said sponge has an antimicrobial efficacy towards *Staphylococcus aureus* of 99.53% or greater than or equal to 99.9%, respectively.

* * * * *